(12) United States Patent
Arana et al.

(10) Patent No.: US 8,657,782 B2
(45) Date of Patent: Feb. 25, 2014

(54) CATHETER HAVING TRANSITIONING SHAFT SEGMENTS

(75) Inventors: Ramon Arana, Temecula, CA (US);
Daniel Brown, Temecula, CA (US);
Curt A. Novak, Corona, CA (US);
Justin K. Mann, Murrieta, CA (US);
John A. Simpson, Carlsbad, CA (US);
Bruce M. Wilson, Temecula, CA (US);
Leonard D. Barbod, San Diego, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/562,810

(22) Filed: Jul. 31, 2012

(65) Prior Publication Data
US 2012/0296273 A1 Nov. 22, 2012

Related U.S. Application Data

(63) Continuation of application No. 11/958,106, filed on Dec. 17, 2007, now Pat. No. 8,403,885.

(51) Int. Cl.
*A61M 29/00* (2006.01)
(52) U.S. Cl.
USPC ................................ 604/96.01; 604/103.06
(58) Field of Classification Search
CPC .................................................... A61M 29/00
USPC ............ 604/96.01, 103, 103.06, 385.12, 509, 604/720, 912
See application file for complete search history.

(56) References Cited

U.S. PATENT DOCUMENTS

| | | | |
|---|---|---|---|
| 4,425,919 A | 1/1984 | Alston, Jr. et al. |
| 4,563,181 A | 1/1986 | Wijayarathna et al. |
| 4,596,563 A | 6/1986 | Pande |
| 4,775,371 A | 10/1988 | Mueller, Jr. |
| 4,820,349 A | 4/1989 | Saab et al. |
| 4,877,031 A | 10/1989 | Conway et al. |
| 4,886,506 A | 12/1989 | Lovgren et al. |
| 4,892,519 A | 1/1990 | Songer et al. |

(Continued)

FOREIGN PATENT DOCUMENTS

| | | |
|---|---|---|
| EP | 0 277 368 A | 8/1988 |
| EP | 0 414 350 A | 2/1991 |

(Continued)

OTHER PUBLICATIONS

U.S. Appl. No. 11/958,106, Nov. 20, 2012, Notice of Allowance.

(Continued)

*Primary Examiner* — Nicholas Lucchesi
*Assistant Examiner* — Gerald Landry, II
(74) *Attorney, Agent, or Firm* — Baker Botts LLP (57) ABSTRACT

A catheter having shaft segments which are joined together by a strong bond providing a low profile shaft section with a flexibility transition and/or a compositional transition. A balloon catheter embodying features of the invention has a distal tip member and a coupling band member surrounding a junction of an inner tubular member of the shaft, and has a gradual change in bending stiffness along a distal end section of the shaft which extends distally from a location within the balloon interior. Another catheter embodying features of the invention has shaft segments joined together by a diagonal seam.

19 Claims, 4 Drawing Sheets

(56) References Cited

U.S. PATENT DOCUMENTS

| | | | |
|---|---|---|---|
| 4,952,357 A | 8/1990 | Euteneuer | |
| 4,960,410 A | 10/1990 | Pinchuk | |
| 4,976,720 A | 12/1990 | Machold et al. | |
| 5,047,045 A | 9/1991 | Arney et al. | |
| 5,061,273 A | 10/1991 | Yock | |
| 5,078,702 A | 1/1992 | Pomeranz | |
| 5,085,649 A | 2/1992 | Flynn | |
| 5,112,304 A | 5/1992 | Barlow et al. | |
| 5,156,594 A | 10/1992 | Keith | |
| 5,176,661 A | 1/1993 | Evard et al. | |
| 5,195,969 A | 3/1993 | Wang et al. | |
| 5,205,822 A | 4/1993 | Johnson et al. | |
| 5,207,700 A | 5/1993 | Euteneuer | |
| 5,217,434 A | 6/1993 | Arney | |
| 5,217,482 A | 6/1993 | Keith | |
| 5,250,059 A | 10/1993 | Andreas et al. | |
| 5,270,086 A | 12/1993 | Hamlin | |
| 5,277,199 A | 1/1994 | DeBois et al. | |
| 5,290,232 A | 3/1994 | Johnson et al. | |
| 5,290,306 A | 3/1994 | Trotta et al. | |
| 5,300,025 A | 4/1994 | Wantink | |
| 5,304,134 A | 4/1994 | Kraus et al. | |
| 5,312,430 A | 5/1994 | Rosenbluth et al. | |
| 5,318,032 A | 6/1994 | Lonsbury et al. | |
| 5,318,526 A | 6/1994 | Cohen | |
| 5,342,386 A | 8/1994 | Trotta | |
| 5,358,486 A | 10/1994 | Saab | |
| 5,364,357 A | 11/1994 | Aase | |
| 5,370,616 A * | 12/1994 | Keith et al. | 604/102.02 |
| 5,378,238 A * | 1/1995 | Peters et al. | 604/99.04 |
| 5,395,336 A | 3/1995 | Barclay et al. | |
| 5,425,712 A | 6/1995 | Goodin | |
| 5,447,497 A | 9/1995 | Sogard et al. | |
| 5,451,233 A | 9/1995 | Yock | |
| 5,454,789 A * | 10/1995 | Burns et al. | 604/99.04 |
| 5,470,315 A | 11/1995 | Adams | |
| 5,476,477 A | 12/1995 | Burns | |
| 5,478,320 A | 12/1995 | Trotta | |
| 5,484,409 A * | 1/1996 | Atkinson et al. | 604/103.03 |
| 5,490,837 A | 2/1996 | Blaeser et al. | |
| 5,496,275 A | 3/1996 | Sirhan et al. | |
| 5,499,980 A | 3/1996 | Euteneuer | |
| 5,512,051 A | 4/1996 | Wang et al. | |
| 5,526,823 A | 6/1996 | Wheeler et al. | |
| 5,538,513 A | 7/1996 | Okajima | |
| 5,545,134 A | 8/1996 | Hilaire et al. | |
| 5,549,552 A | 8/1996 | Peters et al. | |
| 5,554,121 A | 9/1996 | Ainsworth et al. | |
| 5,556,383 A | 9/1996 | Wang et al. | |
| 5,569,195 A | 10/1996 | Saab | |
| 5,587,125 A | 12/1996 | Roychowdhury | |
| 5,599,326 A | 2/1997 | Carter | |
| 5,613,979 A | 3/1997 | Trotta et al. | |
| 5,620,649 A | 4/1997 | Trotta | |
| 5,622,665 A | 4/1997 | Wang | |
| 5,632,760 A | 5/1997 | Sheiban et al. | |
| 5,643,209 A | 7/1997 | Fugoso et al. | |
| 5,658,264 A | 8/1997 | Samson | |
| 5,690,613 A | 11/1997 | Verbeek | |
| 5,728,063 A | 3/1998 | Preissman et al. | |
| 5,743,874 A | 4/1998 | Fischell et al. | |
| 5,743,875 A | 4/1998 | Sirhan et al. | |
| 5,749,849 A | 5/1998 | Engelson | |
| 5,755,690 A | 5/1998 | Saab | |
| 5,759,173 A | 6/1998 | Preissman et al. | |
| 5,766,151 A | 6/1998 | Valley et al. | |
| 5,769,817 A | 6/1998 | Burgmeier | |
| 5,769,819 A | 6/1998 | Schwab et al. | |
| 5,775,327 A | 7/1998 | Randolph et al. | |
| 5,779,731 A | 7/1998 | Leavitt | |
| 5,782,811 A | 7/1998 | Samson et al. | |
| 5,791,036 A | 8/1998 | Goodin et al. | |
| 5,792,124 A | 8/1998 | Horrigan et al. | |
| 5,792,144 A | 8/1998 | Fischell et al. | |
| 5,795,325 A | 8/1998 | Valley et al. | |
| 5,795,341 A | 8/1998 | Samson | |
| 5,797,887 A | 8/1998 | Rosen et al. | |
| 5,814,016 A | 9/1998 | Valley et al. | |
| 5,820,594 A | 10/1998 | Fontirroche et al. | |
| 5,833,657 A | 11/1998 | Reinhardt et al. | |
| 5,879,369 A | 3/1999 | Ishida | |
| 5,879,499 A | 3/1999 | Corvi | |
| 5,902,290 A | 5/1999 | Peacock et al. | |
| 5,908,406 A | 6/1999 | Ostapchenko et al. | |
| 5,911,715 A * | 6/1999 | Berg et al. | 604/525 |
| 5,916,193 A | 6/1999 | Stevens et al. | |
| 5,947,939 A | 9/1999 | Mortier et al. | |
| 5,964,778 A | 10/1999 | Fugoso et al. | |
| 6,004,289 A | 12/1999 | Saab | |
| 6,004,339 A | 12/1999 | Wijay | |
| 6,010,521 A | 1/2000 | Lee et al. | |
| 6,021,340 A | 2/2000 | Randolph et al. | |
| 6,024,693 A | 2/2000 | Schock et al. | |
| 6,024,722 A | 2/2000 | Rau et al. | |
| 6,027,510 A | 2/2000 | Alt | |
| 6,036,670 A | 3/2000 | Wijeratne et al. | |
| 6,056,719 A | 5/2000 | Mickley | |
| 6,059,751 A | 5/2000 | Ostapchenko et al. | |
| 6,059,770 A | 5/2000 | Peacock et al. | |
| 6,071,266 A | 6/2000 | Kelley | |
| 6,086,556 A | 7/2000 | Hamilton et al. | |
| 6,102,890 A | 8/2000 | Stivland et al. | |
| 6,124,007 A | 9/2000 | Wang et al. | |
| 6,132,824 A | 10/2000 | Hamlin | |
| 6,136,258 A | 10/2000 | Wang et al. | |
| 6,146,356 A | 11/2000 | Wang et al. | |
| 6,165,166 A | 12/2000 | Samuelson et al. | |
| 6,165,195 A | 12/2000 | Wilson et al. | |
| 6,168,588 B1 | 1/2001 | Wilson | |
| 6,171,275 B1 | 1/2001 | Webster, Jr. et al. | |
| 6,171,278 B1 | 1/2001 | Wang et al. | |
| 6,179,810 B1 | 1/2001 | Wantink et al. | |
| 6,179,856 B1 | 1/2001 | Barbere | |
| 6,193,686 B1 | 2/2001 | Estrada et al. | |
| 6,197,015 B1 | 3/2001 | Wilson | |
| 6,210,396 B1 | 4/2001 | MacDonald et al. | |
| 6,217,547 B1 | 4/2001 | Lee | |
| 6,217,565 B1 | 4/2001 | Cohen | |
| 6,242,063 B1 | 6/2001 | Ferrera et al. | |
| 6,245,053 B1 | 6/2001 | Benjamin | |
| 6,251,093 B1 | 6/2001 | Valley et al. | |
| 6,264,683 B1 | 7/2001 | Stack et al. | |
| 6,265,016 B1 | 7/2001 | Hostettler et al. | |
| 6,306,097 B1 | 10/2001 | Park et al. | |
| 6,306,124 B1 | 10/2001 | Jones et al. | |
| 6,308,342 B1 | 10/2001 | Qi | |
| 6,358,227 B1 | 3/2002 | Ferrera et al. | |
| 6,364,894 B1 | 4/2002 | Healy et al. | |
| 6,402,720 B1 | 6/2002 | Miller et al. | |
| 6,416,494 B1 | 7/2002 | Wilkins | |
| 6,482,348 B1 | 11/2002 | Wang et al. | |
| 6,495,090 B1 | 12/2002 | Wilkins et al. | |
| 6,495,127 B1 | 12/2002 | Wallace et al. | |
| 6,500,148 B1 | 12/2002 | Pinchuk et al. | |
| 6,508,784 B1 | 1/2003 | Shu | |
| 6,530,938 B1 | 3/2003 | Lee et al. | |
| 6,575,934 B2 | 6/2003 | Duchamp | |
| 6,575,958 B1 | 6/2003 | Happ et al. | |
| 6,579,259 B2 | 6/2003 | Stevens et al. | |
| 6,585,687 B1 | 7/2003 | Shkolnik | |
| 6,585,688 B2 | 7/2003 | Ferrera et al. | |
| 6,589,207 B1 | 7/2003 | El-Nounou | |
| 6,589,226 B1 | 7/2003 | Owens | |
| 6,591,472 B1 | 7/2003 | Noon et al. | |
| 6,620,127 B2 | 9/2003 | Lee et al. | |
| 6,620,128 B1 | 9/2003 | Simhambhatla | |
| 6,626,889 B1 | 9/2003 | Simpson et al. | |
| 6,629,961 B1 | 10/2003 | Israelsson et al. | |
| 6,645,422 B2 | 11/2003 | Jung, Jr. et al. | |
| 6,663,614 B1 | 12/2003 | Carter | |
| 6,673,291 B1 | 1/2004 | Field et al. | |
| 6,673,302 B2 | 1/2004 | Wang et al. | |
| 6,695,809 B1 | 2/2004 | Lee | |
| 6,702,802 B1 | 3/2004 | Hancock et al. | |

(56) References Cited

U.S. PATENT DOCUMENTS

| | | | |
|---|---|---|---|
| 6,718,211 B2 | 4/2004 | Smits |
| 6,733,487 B2 | 5/2004 | Keith et al. |
| 6,756,094 B1 | 6/2004 | Wang et al. |
| 6,777,644 B2 | 8/2004 | Peacock et al. |
| 6,793,647 B1 | 9/2004 | Cryer et al. |
| 6,796,958 B2 | 9/2004 | Chen et al. |
| 6,796,960 B2 | 9/2004 | Cioanta et al. |
| 6,835,189 B2 | 12/2004 | Musbach et al. |
| 6,837,890 B1 | 1/2005 | Chludzinski et al. |
| 6,863,678 B2 | 3/2005 | Lee et al. |
| 6,875,197 B1 | 4/2005 | Simhambhatla et al. |
| 6,887,219 B2 | 5/2005 | Wantink |
| 6,890,395 B2 | 5/2005 | Simhambhatla et al. |
| 6,893,456 B2 | 5/2005 | Lumauig |
| 6,911,038 B2 | 6/2005 | Mertens et al. |
| 6,913,600 B2 | 7/2005 | Valley et al. |
| 6,918,920 B1 | 7/2005 | Wang et al. |
| 6,946,092 B1 | 9/2005 | Bertolino et al. |
| 6,951,555 B1 | 10/2005 | Suresh et al. |
| 6,951,675 B2 | 10/2005 | Chin et al. |
| 6,979,342 B2 | 12/2005 | Lee et al. |
| 7,026,026 B2 | 4/2006 | Ferrera et al. |
| 7,029,732 B2 | 4/2006 | Wang et al. |
| 7,037,291 B2 | 5/2006 | Lee et al. |
| 7,037,295 B2 | 5/2006 | Tieman et al. |
| 7,074,206 B2 | 7/2006 | Lee et al. |
| 7,108,877 B2 | 9/2006 | Blair et al. |
| 7,112,357 B2 | 9/2006 | Miller et al. |
| 7,141,059 B2 | 11/2006 | Duchamp et al. |
| 7,147,817 B1 | 12/2006 | Lim et al. |
| 7,163,523 B2 | 1/2007 | Devens, Jr. et al. |
| 7,195,638 B1 | 3/2007 | Sridharan |
| 7,273,485 B2 | 9/2007 | Simpson et al. |
| 7,335,185 B2 | 2/2008 | Tang et al. |
| 7,341,571 B1 | 3/2008 | Harris et al. |
| 7,556,634 B2 | 7/2009 | Lee et al. |
| 7,662,130 B2 | 2/2010 | Lee et al. |
| 7,833,193 B2 | 11/2010 | Lee et al. |
| 7,906,066 B2 | 3/2011 | Wilson et al. |
| 7,947,059 B2 | 5/2011 | Chin et al. |
| 8,012,300 B2 | 9/2011 | Simpson et al. |
| 8,052,638 B2 | 11/2011 | Lee et al. |
| 8,070,719 B2 | 12/2011 | Lee et al. |
| 8,382,738 B2 | 2/2013 | Simpson et al. |
| 2001/0001812 A1 | 5/2001 | Valley et al. |
| 2001/0016702 A1 | 8/2001 | Benjamin |
| 2001/0029362 A1 | 10/2001 | Sirhan et al. |
| 2001/0037085 A1 | 11/2001 | Keith et al. |
| 2002/0018866 A1 | 2/2002 | Lee et al. |
| 2002/0072755 A1* | 6/2002 | Bigus et al. ............ 606/108 |
| 2002/0165523 A1 | 11/2002 | Chin et al. |
| 2003/0009151 A1 | 1/2003 | Wang |
| 2003/0032920 A1 | 2/2003 | Wantink |
| 2003/0055447 A1 | 3/2003 | Lee et al. |
| 2003/0105426 A1 | 6/2003 | Jorgensen |
| 2003/0125712 A1 | 7/2003 | Zhou |
| 2003/0139762 A1 | 7/2003 | Lee |
| 2004/0059291 A1 | 3/2004 | McDonnell et al. |
| 2004/0059292 A1 | 3/2004 | Hisamatsu et al. |
| 2004/0064130 A1 | 4/2004 | Carter |
| 2004/0068240 A1 | 4/2004 | Goodin et al. |
| 2004/0097892 A1 | 5/2004 | Evans et al. |
| 2004/0131808 A1 | 7/2004 | Schoenie et al. |
| 2004/0167441 A1 | 8/2004 | Reynolds et al. |
| 2004/0170782 A1 | 9/2004 | Wang et al. |
| 2004/0173935 A1 | 9/2004 | Lim et al. |
| 2004/0181206 A1 | 9/2004 | Chiu et al. |
| 2004/0191443 A1 | 9/2004 | Hamlin |
| 2004/0215141 A1 | 10/2004 | Clarke et al. |
| 2004/0267195 A1 | 12/2004 | Currlin |
| 2004/0267280 A1 | 12/2004 | Nishide et al. |
| 2005/0015048 A1 | 1/2005 | Chiu et al. |
| 2005/0043679 A1 | 2/2005 | Devens et al. |
| 2005/0124976 A1 | 6/2005 | Devens et al. |
| 2005/0131445 A1 | 6/2005 | Holman et al. |
| 2005/0148997 A1 | 7/2005 | Valley et al. |
| 2005/0154414 A1 | 7/2005 | Perreault et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0277878 A1 | 12/2005 | Lee |
| 2006/0008606 A1 | 1/2006 | Horn et al. |
| 2006/0136032 A1 | 6/2006 | Legarda et al. |
| 2006/0165926 A1 | 7/2006 | Weber |
| 2006/0175739 A1 | 8/2006 | Hession et al. |
| 2006/0282041 A1 | 12/2006 | Melsheimer et al. |
| 2007/0060863 A1 | 3/2007 | Goeken et al. |
| 2007/0142771 A1 | 6/2007 | Durcan |
| 2007/0167973 A1 | 7/2007 | Stupecky et al. |
| 2007/0191813 A1 | 8/2007 | Chen |
| 2007/0240817 A1 | 10/2007 | Strong et al. |
| 2008/0045895 A1 | 2/2008 | Simpson et al. |
| 2008/0045928 A1 | 2/2008 | Simpson et al. |
| 2008/0065188 A1 | 3/2008 | Pallazza |
| 2008/0262470 A1 | 10/2008 | Lee et al. |
| 2009/0005754 A1 | 1/2009 | Soetermans |
| 2009/0156998 A1 | 6/2009 | Arana et al. |
| 2009/0247946 A1 | 10/2009 | Lee et al. |
| 2009/0264822 A1 | 10/2009 | Johnson |
| 2010/0010439 A1 | 1/2010 | Burgmeier et al. |
| 2010/0130925 A1 | 5/2010 | Haslinger et al. |
| 2011/0315301 A1 | 12/2011 | Simpson et al. |
| 2012/0065586 A1 | 3/2012 | Lee et al. |
| 2012/0143129 A1 | 6/2012 | Simpson et al. |
| 2013/0253425 A1 | 9/2013 | Haslinger et al. |

FOREIGN PATENT DOCUMENTS

| | | |
|---|---|---|
| EP | 0 420 488 A | 3/1991 |
| EP | 0 737 487 A | 10/1996 |
| EP | 0 821 979 A | 2/1998 |
| EP | 0 904 795 A | 3/1999 |
| EP | 0 931 558 A | 7/1999 |
| EP | 0 962 227 A | 12/1999 |
| EP | 1 103 280 A | 5/2001 |
| EP | 1 287 846 A | 3/2003 |
| JP | 10-290837 | 11/1998 |
| JP | 2001-018290 | 1/2001 |
| JP | 2001-353225 | 12/2001 |
| JP | 2005-167638 | 6/2005 |
| WO | WO 89/02763 | 4/1989 |
| WO | WO 93/20882 | 10/1993 |
| WO | WO 95/18647 | 7/1995 |
| WO | WO 96/03175 | 2/1996 |
| WO | WO 96/34646 | 11/1996 |
| WO | WO 97/26027 | 7/1997 |
| WO | WO 99/13924 | 3/1999 |
| WO | WO 01/34240 | 5/2001 |
| WO | WO 01/51115 | 7/2001 |
| WO | WO 01/89621 | 11/2001 |
| WO | WO 02/36196 | 5/2002 |
| WO | WO 03/004248 | 1/2003 |
| WO | WO 2005/021083 | 3/2005 |
| WO | WO 2006/126311 | 11/2006 |
| WO | WO 2007/054364 | 5/2007 |
| WO | WO 2007/146572 | 12/2007 |

OTHER PUBLICATIONS

U.S. Appl. No. 13/240,453, Dec. 5, 2012, Non-Final Office Action.
U.S. Appl. No. 13/775,699, filed Feb. 25, 2013.
U.S. Appl. No. 13/775,659, filed Feb. 5, 2013.
U.S. Appl. No. 12/478,929, Apr. 18, 2013 Issue Fee payment.
U.S. Appl. No. 13/240,453, Apr. 30, 2013 Response to Non-Final Office Action.
U.S. Appl. No. 13/562,810, filed Jul. 31, 2012.
U.S. Appl. No. 11/480,143, Feb. 3, 2011 Issue Fee payment.
U.S. Appl. No. 11/480,143, Nov. 18, 2010 Notice of Allowance.
U.S. Appl. No. 11/480,143, Aug. 23, 2010 Response to Non-Final Office Action.
U.S. Appl. No. 11/480,143, Apr. 22, 2010 Non-Final Office Action.
U.S. Appl. No. 11/480,143, Feb. 18, 2010 Amendment and Request for Continued Examination (RCE).

(56) References Cited

OTHER PUBLICATIONS

U.S. Appl. No. 11/480,143, Feb. 4, 2010 Advisory Action.
U.S. Appl. No. 11/480,143, Jan. 15, 2010 Response to Final Office Action.
U.S. Appl. No. 11/480,143, Aug. 18, 2009 Final Office Action.
U.S. Appl. No. 11/480,143, May 27, 2009 Response to Non-Final Office Action.
U.S. Appl. No. 11/480,143, Jan. 27, 2009 Non-Final Office Action.
U.S. Appl. No. 11/763,623, Aug. 24, 2010 Amendment and Request for Continued Examination (RCE).
U.S. Appl. No. 11/763,623, May 24, 2010 Notice of Appeal.
U.S. Appl. No. 11/763,623, Feb. 23, 2010 Final Office Action.
U.S. Appl. No. 11/763,623, Jan. 15, 2010 Response to Non-Final Office Action.
U.S. Appl. No. 11/763,623, Oct. 15, 2009 Non-Final Office Action.
U.S. Appl. No. 11/763,623, Jul. 20, 2009 Amendment and Request for Continued Examination (RCE).
U.S. Appl. No. 11/763,623, Mar. 20, 2009 Final Office Action.
U.S. Appl. No. 11/763,623, Mar. 3, 2009 Response to Non-Final Office Action.
U.S. Appl. No. 11/763,623, Dec. 3, 2008 Non-Final Office Action.
U.S. Appl. No. 11/958,106, Aug. 1, 2012 Non-Final Office Action.
U.S. Appl. No. 11/958,106, May 29, 2012 Response to Non-Compliant.
U.S. Appl. No. 11/958,106, May 17, 2012 Notice of Non-Compliant.
U.S. Appl. No. 11/958,106, May 7, 2012 Response to Non-Final Office Action.
U.S. Appl. No. 11/958,106, Jan. 6, 2012 Non-Final Office Action.
U.S. Appl. No. 11/958,106, Jun. 17, 2010 Amendment and Request for Continued Examination (RCE).
U.S. Appl. No. 11/958,106, Mar. 17, 2010 Final Office Action.
U.S. Appl. No. 11/958,106, Jan. 8, 2010 Response to Non-Final Office Action.
U.S. Appl. No. 11/958,106, Jul. 8, 2009 Non-Final Office Action.
U.S. Appl. No. 09/957,526, Jan. 24, 2005 Issue Fee payment.
U.S. Appl. No. 09/957,526, Nov. 4, 2004 Notice of Allowance.
U.S. Appl. No. 09/957,526, Sep. 21, 2004 Response to Non-Final Office Action.
U.S. Appl. No. 09/957,526, Jul. 1, 2004 Non-Final Office Action.
U.S. Appl. No. 09/957,526, Apr. 22, 2004 Amendment and Request for Continued Examination (RCE).
U.S. Appl. No. 09/957,526, Feb. 17, 2004 Final Office Action.
U.S. Appl. No. 09/957,526, Nov. 26, 2003 Response to Non-Final Office Action.
U.S. Appl. No. 09/957,526, Jun. 23, 2003 Non-Final Office Action.
U.S. Appl. No. 11/038,971, May 29, 2009 Issue Fee payment.
U.S. Appl. No. 11/038,971, Mar. 13, 2009 Notice of Allowance.
U.S. Appl. No. 11/038,971, Sep. 19, 2008 Response to Non-Final Office Action.
U.S. Appl. No. 11/038,971, Jul. 29, 2008 Non-Final Office Action.
U.S. Appl. No. 11/038,971, Feb. 28, 2008 Response to Non-Final Office Action.
U.S. Appl. No. 11/038,971, Nov. 28, 2007 Non-Final Office Action.
U.S. Appl. No. 11/038,971, Sep. 18, 2007 Response to Non-Final Office Action.
U.S. Appl. No. 11/038,971, Jun. 28, 2007 Non-Final Office Action.
U.S. Appl. No. 11/038,971, Apr. 12, 2007 Amendment and Request for Continued Examination (RCE).
U.S. Appl. No. 11/038,971, Feb. 16, 2007 Final Office Action.
U.S. Appl. No. 11/038,971, Nov. 13, 2006 Response to Non-Final Office Action.
U.S. Appl. No. 11/038,971, Sep. 21, 2006 Non-Final Office Action.
U.S. Appl. No. 12/477,695, Apr. 16, 2012 Response to Non-Final Office Action.
U.S. Appl. No. 12/477,695, Dec. 16, 2011 Non-Final Office Action.
U.S. Appl. No. 10/392,697, Aug. 22, 2007 Issue Fee payment.
U.S. Appl. No. 10/392,697, May 31, 2007 Notice of Allowance.
U.S. Appl. No. 10/392,697, Feb. 26, 2007 Amendment and Request for Continued Examination (RCE).
U.S. Appl. No. 10/392,697, Jan. 5, 2007 Final Office Action.
U.S. Appl. No. 10/392,697, Sep. 29, 2006 Response to Non-Final Office Action.
U.S. Appl. No. 10/392,697, Jul. 13, 2006 Non-Final Office Action.
U.S. Appl. No. 11/844,117, Aug. 2, 2011 Issue Fee payment.
U.S. Appl. No. 11/844,117, Jun. 15, 2011 Notice of Allowance.
U.S. Appl. No. 11/844,117, Mar. 23, 2011 Response to Non-Final Office Action.
U.S. Appl. No. 11/844,117, Nov. 23, 2010 Non-Final Office Action.
U.S. Appl. No. 11/844,117, Nov. 17, 2010 Amendment and Request for Continued Examination (RCE).
U.S. Appl. No. 11/844,117, Aug. 17, 2010 Final Office Action.
U.S. Appl. No. 11/844,117, Jun. 30, 2010 Response to Non-Compliant.
U.S. Appl. No. 11/844,117, Jun. 23, 2010 Notice of Non-Compliant.
U.S. Appl. No. 11/844,117, Jun. 17, 2010 Response to Non-Final Office Action.
U.S. Appl. No. 11/844,117, Mar. 17, 2010 Non-Final Office Action.
U.S. Appl. No. 10/010,212, Mar. 6, 2006 Issue Fee payment.
U.S. Appl. No. 10/010,212, Feb. 9, 2006 Notice of Allowance.
U.S. Appl. No. 10/010,212, Dec. 27, 2005 Response to Final Office Action.
U.S. Appl. No. 10/010,212, Oct. 19, 2005 Final Office Action.
U.S. Appl. No. 10/010,212, Aug. 4, 2005 Response to Non-Final Office Action.
U.S. Appl. No. 10/010,212, May 6, 2005 Non-Final Office Action.
U.S. Appl. No. 10/010,212, Feb. 4, 2005 Amendment and Request for Continued Examination (RCE).
U.S. Appl. No. 10/010,212, Dec. 2, 2004 Final Office Action.
U.S. Appl. No. 10/010,212, Aug. 9, 2004 Response to Non-Final Office Action.
U.S. Appl. No. 10/010,212, Jun. 16, 2004 Non-Final Office Action.
U.S. Appl. No. 10/010,212, Mar. 22, 2004 Response to Non-Final Office Action.
U.S. Appl. No. 10/010,212, Dec. 31, 2003 Non-Final Office Action.
U.S. Appl. No. 10/010,212, Oct. 14, 2003 Amendment and Request for Continued Examination (RCE).
U.S. Appl. No. 10/010,212, Jul. 7, 2003 Final Office Action.
U.S. Appl. No. 10/010,212, Apr. 18, 2003 Response to Non-Final Office Action.
U.S. Appl. No. 10/010,212, Jan. 15, 2003 Non-Final Office Action.
U.S. Appl. No. 11/196,134, Dec. 29, 2009 Issue Fee payment.
U.S. Appl. No. 11/196,134, Sep. 30, 2009 Notice of Allowance.
U.S. Appl. No. 11/196,134, Sep. 10, 2009 Amendment and Request for Continued Examination (RCE).
U.S. Appl. No. 11/196,134, Jun. 10, 2009 Final Office Action.
U.S. Appl. No. 11/196,134, Mar. 24, 2009 Response to Non-Final Office Action.
U.S. Appl. No. 11/196,134, Dec. 24, 2008 Non-Final Office Action.
U.S. Appl. No. 12/687,265, Oct. 14, 2010 Issue Fee payment.
U.S. Appl. No. 12/687,265, Aug. 5, 2010 Notice of Allowance.
U.S. Appl. No. 12/324,425, Oct. 31, 2011 Amendment after Notice of Allowance.
U.S. Appl. No. 12/324,425, Sep. 22, 2011 Issue Fee payment.
U.S. Appl. No. 12/324,425, Aug. 31, 2011 Notice of Allowance.
U.S. Appl. No. 12/324,425, Jun. 6, 2011 Response to Non-Final Office Action.
U.S. Appl. No. 12/324,425, Mar. 4, 2011 Non-Final Office Action.
U.S. Appl. No. 12/479,700, Sep. 22, 2011 Issue Fee payment.
U.S. Appl. No. 12/479,700, Aug. 22, 2011 Notice of Allowance.
U.S. Appl. No. 12/479,700, May 20, 2011 Response to Interview Summary and Non-Final Office Action.
U.S. Appl. No. 12/479,700, Apr. 27, 2011 Response to Non-Final Office Action.
U.S. Appl. No. 12/479,700, Oct. 27, 2010 Non-Final Office Action.
U.S. Appl. No. 12/478,929, Jun. 20, 2012 Non-Final Office Action.
U.S. Appl. No. 12/478,929, Jul. 18, 2011 Request for Continued Examination (RCE).
U.S. Appl. No. 12/478,929, Jul. 13, 2011 Advisory Action.
U.S. Appl. No. 12/478,929, Jun. 6, 2011 Response to Final Office Action.
U.S. Appl. No. 12/478,929, Mar. 4, 2011 Final Office Action.
U.S. Appl. No. 12/478,929, Dec. 9, 2010 Response to Non-Final Office Action.

(56) References Cited

OTHER PUBLICATIONS

U.S. Appl. No. 12/478,929, Jul. 9, 2010 Non-Final Office Action.
Cordis' Product Brochure; The Journey Inspires the Design, AQUA T3, Dec. 2002.
The Manufacturing Process Section of the Phelps Dodge High Performance Conductors Brochure, a Primer on Polymide Tubing, pp. 1.
http://www.zeusinc.com/peek_resin.asp.
www.sigmaaldrich.com/img/assets/3900/Thermal_Transitions_of_Homopolymers.pdf.
Etherington & Roberts Dictionary, http://Palimpsest.stanford.edu/don/dt/dt1549.html.
Polymers: Structure and Properties, C.A. Daniels, Ph.D., P.E.; Technomic Publishing Co., Inc.
International Search Report for PCT/US2007/071873, dated Apr. 14, 2008.
International Search Report for PCT/US2008/086270, dated Jun. 3, 2009.
International Search Report for PCT/US2010/037313, dated Apr. 28, 2011.
U.S. Appl. No. 12/478,929, Sep. 24, 2012 Response to Non-Final Office Action.
U.S. Appl. No. 11/958,106, Oct. 23, 2012 Response to Non-Final Office Action.
U.S. Appl. No. 13/398,178, Oct. 25, 2012 Notice of Allowance.
U.S. Appl. No. 12/477,695, Oct. 24, 2012 Advisory Action.
U.S. Appl. No. 12/477,695, Oct. 24, 2012 Response to Final Office Action.
U.S. Appl. No. 12/477,695, Aug. 15, 2012 Final Office Action.
U.S. Appl. No. 13/224,917, Oct. 12, 2012 Non-Final Office Action.
U.S. Appl. No. 11/763,623, Oct. 29, 2012 Notice of Allowance.
U.S. Appl. No. 11/763,623, Jan. 29, 2013 Issue Fee payment.
U.S. Appl. No. 13/398,178, Jan. 25, 2013 Issue Fee payment.
U.S. Appl. No. 12/478,929, Jan. 18, 2013 Notice of Allowance.
U.S. Appl. No. 12/477,695, Jan. 15, 2013 Amendment and Request for Continued Examination (RCE).
U.S. Appl. No. 13/224,917, Jan. 14, 2013 Response to Non-Final Office Action.
U.S. Appl. No. 13/240,453, Aug. 20, 2013 Notice of Allowance.
U.S. Appl. No. 13/224,917, Sep. 12, 2013 Non-Final Office Action.
U.S. Appl. No. 13/224,917, Aug. 23, 2013 Amendment and Request for Continued Examination (RCE).
U.S. Appl. No. 13/224,917, May 28, 2013 Final Office Action.
U.S. Appl. No. 12/477,695, Sep. 20, 2013 Response to Non-Final Office Action.
U.S. Appl. No. 12/477,695, Jun. 20, 2013 Non-Final Office Action.

\* cited by examiner

CATHETER HAVING TRANSITIONING SHAFT SEGMENTS

CROSS-REFERENCES TO RELATED APPLICATIONS

This application is a continuation of U.S. patent application Ser. No. 11/958,106 entitled, "Catheter Having Transitioning Shaft Segments" and filed Dec. 17, 2007 now U.S. Pat. No. 8,403,885, the contents of which is hereby incorporated by reference in its entirety herein.

BACKGROUND OF THE INVENTION

This invention generally relates to catheters, and particularly intravascular catheters for use in percutaneous transluminal coronary angioplasty (PICA) or for the delivery of stents.

In percutaneous transluminal coronary angioplasty (PTCA) procedures, a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed there from.

In such angioplasty procedures, there may be restenosis of the artery, i.e., reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. For details of stents, see for example, U.S. Pat. No. 5,507,768 (Lau, et al.) and U.S. Pat. No. 5,458,615 (Klemm, et al.), which are incorporated herein by reference.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter), and good trackability and flexibility, to be readily advanceable within the tortuous anatomy of the patient's vasculature. Conventional balloon catheters for intravascular procedures, such as angioplasty and stent delivery, frequently have a relatively stiff proximal shaft section to facilitate advancement of the catheter within the patient's body lumen and a relatively flexible distal shaft section to facilitate passage through tortuous anatomy such as distal coronary and neurological arteries without damage to the vessel wall. These flexibility transitions can be achieved by a number of methods, including bonding two or more segments of different flexibility together to form the shaft. However, such transition bonds must be sufficiently strong to withstand the pulling and pushing forces on the shaft during use. One difficulty has been providing a flexibility transition which improves catheter maneuverability, yet with a sufficiently strong transition bond, especially at the transition between the distal end of the shaft inner tubular member (extending through the balloon interior) and a soft distal tip member formed of a relatively soft material to provide an atraumatic distal leading end for the catheter. If the tip pull strength is low, the soft distal tip member could tear or become detached during use, which can result in serious harm or death to the patient. Moreover, the need for high tip pull strength often competes with the desire for a low tip crossing profile, i.e., efforts to increase the strength of the bond between the soft distal tip member and the balloon and/or inner tubular member often result in an increased distal seal profile. Accordingly, it would be a significant advance to provide a catheter having an improved flexibility transition with a low profile.

SUMMARY OF THE INVENTION

The invention is directed to a catheter having shaft segments which are joined together by a strong bond providing a low profile shaft section with a flexibility transition and/or a compositional transition.

In a presently preferred embodiment, the catheter is a balloon catheter with a balloon on a distal shaft section, having an interior in fluid communication with the at least one lumen of the catheter shaft. A balloon catheter of the invention generally comprises an elongated shaft having a proximal shaft section, a distal shaft section, an inflation lumen extending within the proximal and distal shaft sections, and a guidewire receiving lumen extending at least within the distal shaft section, and an inflatable balloon on the distal shaft section with an interior in fluid communication with the inflation lumen. The balloon typically has a proximal skirt section and a distal skirt section sealingly secured to the shaft, and an inflatable working length and proximal and distal cone sections defining the inflatable interior of the balloon located between the skirt sections of the balloon. In a presently preferred embodiment, the shaft comprises an outer tubular member defining the inflation lumen, and an inner tubular member defining at least a portion of the guidewire receiving lumen. However, a variety of suitable shaft designs may be used including a single-lumen shaft, or eccentric multi-lumen type shafts such as a catheter having the balloon proximal skirt section bonded to the distal end of a dual-lumen type shaft, and the balloon distal skirt section bonded to the distal end of an inner tubular member extending from the distal end of the dual lumen shaft. The balloon catheter of the invention may comprise a variety of suitable balloon catheters, including coronary and peripheral dilatation catheters, stent delivery catheters, drug delivery catheters, and the like.

In one embodiment, a balloon catheter of the invention has a distal tip member and a coupling band member surrounding a junction of the shaft inner tubular member, and has a gradual change in bending stiffness along a distal end section of the shaft which extends distally from a location within the balloon interior. Specifically, the balloon catheter has a distal tip member which is secured to a distal end of the inner tubular member (i.e., the portion of the shaft extending in the balloon interior) to define a distal end section of the shaft lumen, and a distal coupling band member on an outer surface of the inner tubular member surrounding a junction of the inner tubular member, having a distal end which abuts the inner surface of the balloon at a distal end of the distal cone section of the balloon. The distal coupling band member preferably abuts but does not bond to the interior surface of the distal cone section of the balloon, and consequently preferably improves tip pull strength without damaging or otherwise weakening the integrity of the balloon wall. The coupling band member preferably has a low profile, to minimize the shaft profile therealong. In one embodiment, the tip member is a soft distal tip formed at least in part of a softer polymeric material (e.g., having a lower Shore durometer hardness) than the distal end of the shaft inner tubular member.

In another embodiment, a catheter of the invention has shaft segments joined together by a diagonal seam, and generally comprises an elongated shaft having a proximal end, a distal end, a proximal tubular member, and a distal tubular member which has a diagonally extending proximal end bonded to a diagonally extending distal end of the proximal tubular member, such that the bond between the ends extends from a first side of the shaft diagonally to an opposite side of the shaft (i.e., diagonally across the lumen defined by the tubular members) to form a diagonal seam. The diagonal seam can be used to join a soft tip member to the shaft inner member, or additionally or alternatively to join more proximal shaft segments together.

Although discussed primarily in terms of a junction between different stiffness tubular members providing a flexibility transition, it should be understood that the junctions of the invention can additionally or alternatively provide a change in the composition of the shaft in order to change different shaft characteristics such as bondability, lubricity, radiopacity, color, and the like.

A catheter of the invention has an improved transition, such as a flexibility transition along a length of the catheter shaft which preferably provides improved trackability. These and other advantages of the invention will become more apparent from the following detailed description and accompanying exemplary drawings.

DETAILED DESCRIPTION OF THE PREFERRED EMBODIMENTS

Figure 1:
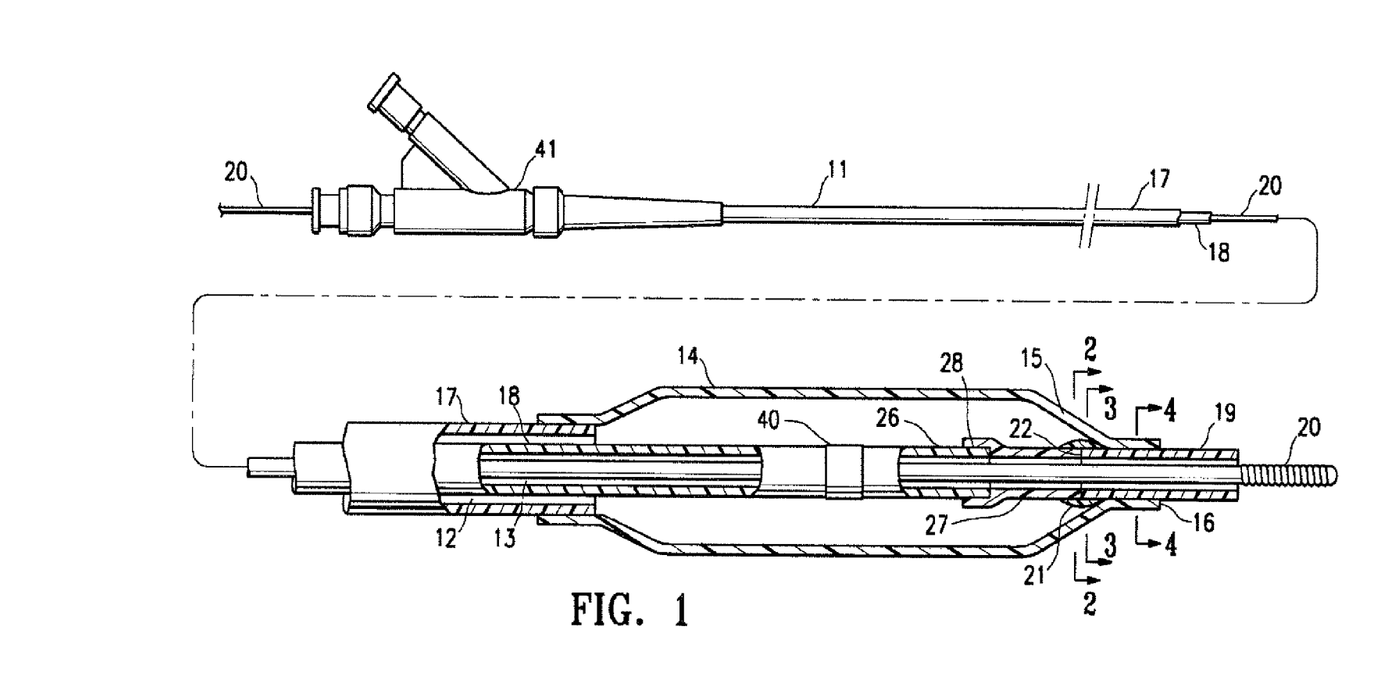
FIG. 1 is an elevational view, partially in section, of a balloon catheter embodying features of the invention, having a distal coupling band member surrounding a junction between an inner tubular member and a distal tip member.

FIG. 1 illustrates an elevational view, partially in section, of a balloon catheter 10 embodying features of the invention, generally comprising an elongated shaft 11 having a proximal end, a distal end, an inflation lumen 12, a guidewire receiving lumen 13, and a balloon 14 on a distal shaft section having an inflatable working length between an inflatable proximal cone section and an inflatable distal cone section 15, and a proximal skirt section and distal skirt section 16 sealingly secured to the shaft, such that an interior of the balloon is in fluid communication with the inflation lumen 12. In the illustrated embodiment the shaft 11 comprises an outer tubular member 17 with the inflation lumen 12 therein, and an inner tubular member 18 with the guidewire lumen 13 therein, and a distal tip member 19 is secured to a distal end of the inner tubular member 18 to define a distal end section of the guidewire lumen. A radiopaque marker band 40 of metal or radiopaque loaded polymer is on the inner tubular member at about the center of the working length of the balloon, although radiopaque markers can be provided at a variety of locations including at the ends of the working length section. An adapter 41 on the distal end of the shaft has a port configured for connecting to a fluid delivery source (not shown) for inflating/deflating the balloon 14. The catheter 10 can be advanced within a patient's vasculature to position the balloon 14 at a desired location with the balloon in a low profile deflated configuration, and the balloon inflated to perform a medical procedure one or more times, and the balloon deflated for removal from the patient. FIG. 1 illustrates the balloon in an inflated configuration, with a guidewire 20 slidably disposed in the guidewire lumen 13.

In the embodiment of FIG. 1, the inner tubular member 18 comprises a proximal member 26, and a distal member 27 which has a proximal end bonded to a distal end of the proximal member 26, and which forms the distal end of the inner tubular member bonded to the distal tip member 19. Typically, the distal member 27 of the inner tubular member is more flexible than the proximal member 26, to improve the ability of the catheter to track along the guidewire 20 and be advanced within a patient's tortuous anatomy. The distal tip member 19 is typically formed of a relatively soft polymeric material providing an atraumatic distal leading end, and in one embodiment, is formed at least in part of a softer polymeric material than the distal end section of the inner tubular member immediately proximally adjacent to the soft distal tip member 19. The soft distal tip member 19 can be formed of a variety of suitable polymeric materials, although at least the outer surface is preferably fusion bond compatible with the material of the balloon 14. The relatively low Shore durometer hardness of the soft distal tip material is typically about 35 to about 70D. In the embodiment of FIG. 1, a proximal end of the distal tip member 19 is located in the balloon inflatable interior proximal to the distal skirt section 16, and the distal skirt section 16 is sealingly secured to an outer surface of (only) the distal tip member 19.

Figure 2:
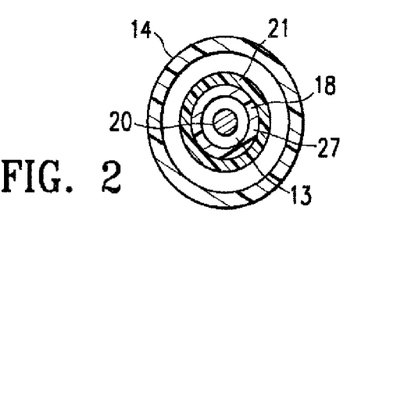
FIGS. 2-4 are transverse cross sectional views of the catheter of FIG. 1, taken along lines 2-2, 3-3 and 4-4, respectively.
Figure 3:
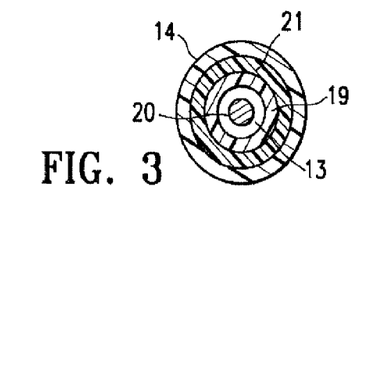
Figure 4:
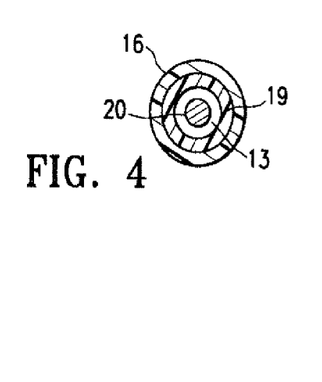

A distal coupling band member 21 on an outer surface of the inner tubular member 18 surrounds a junction 22 of the inner tubular member 18, and has a distal end which abuts the inner surface of the balloon 14 at a distal end of the distal cone section 15. The junction surrounded by the distal coupling band member 21 is between the distal end of the inner tubular member 18 and the proximal end of the distal tip member 19. Specifically, the distal tip member 19 and the distal member 27 of the inner tubular member 18 are bonded end-to-end, with the distal coupling band member surrounding the abutting ends of the tubular members. The distal coupling band member 21 is formed of a polymeric material, and has an inner surface bonded to the outer surfaces of the inner tubular member 18 and distal tip member 19 across the junction 22, to strengthen the junction. The distal coupling band member is preferably fusion bonded to the outer surfaces of the shaft members 18, 19. Additionally, at least a layer of the inner tubular member 18 fusion bonds to the abutting end of the distal tip 19 to form the junction 22. Although adhesive bonding is possible it is much less preferred due at least in part to manufacturing complications. FIGS. 2-4 are transverse cross sectional views of the catheter of FIG. 1, taken along lines 2-2, 3-3 and 4-4, respectively.

The distal coupling band member 21 is not bonded to the balloon 14. Thus, the outer end surface of the distal coupling band member 21 that abuts the inner surface of the distal cone of the balloon is not bonded to said inner surface of the balloon. Preferably, to prevent such bonding from occurring, the distal cone of the balloon is cooled during heat fusion bonding of the distal skirt section of the balloon to the underlying section of the distal tip member 19, for example by directing a cooling fluid (e.g., air stream) at the distal cone. The coupling band member 21 preferably has a low profile, and specifically, in one embodiment is about 0.03 to about 0.07 mm thick. However, the coupling band member 21 is configured to provide a moderate profile increase sufficient to prevent pullout to improve tip pull strength, and is thus unlike conventional thin metal marker bands commonly embedded in the shaft to minimize any local profile increase. Although the coupling band member 21 is thin, it preferably does not extend under the distal skirt section 16 of the balloon. Prior to bonding, the distal skirt section 16 of the balloon has an inner diameter closely matched to the outer diameter of the section of the shaft (e.g., the distal tip member 19) to be bonded thereto, such that the resulting distal skirt section seal has a low profile. During assembly, the distal tip member 19 is slid distally through the distal skirt section until the distal coupling band member, preferably acting as a stop, abuts the inner surface of the distal cone. With the distal tip member 19 thus in position under the distal skirt 16, the bond between the distal skirt 16 and distal tip 19 is formed. In the resulting finished catheter, the distal coupling band member increases the tip pull strength (i.e., the ability of the catheter at the distal tip 19 to withstand pushing and pulling forces).

The polymeric material of the distal coupling band member 21 can melt and flow during bonding to the shaft 11. However, the bulk of the material of the distal coupling band member 21 must remain over the inner member junction 22 for functioning as the required coupler, and for preferably acting as a stop which abuts the inner surface of the inflatable cone 15 of the balloon 14. Thus, the distal coupling band member 21 preferably does not extend under the distal skirt section 16 of the balloon 14, or otherwise does not substantially increase the profile at the distal skirt 16 (e.g., by no more than 0.0005 to about 0.002 inches, or about 2 to about 10% of the outer diameter at the distal skirt 16).

The distal coupling band member 21 has a relatively short length configured to provide sufficient strengthening of the junction 22 while minimizing the length (to minimize any stiffness/profile disadvantageous effects), thus, in one embodiment the proximal end of the distal coupling band member 21 is located closer to the distal end of the distal cone section 15 than to a proximal end of the distal cone section 15 of the balloon 14. However, depending on the size of the balloon, the proximal end of the distal coupling band member 21 could be anywhere along the length of the distal cone of the balloon. The distal coupling band member 21 length is typically about 1 to about 3 mm.

Figure 5:
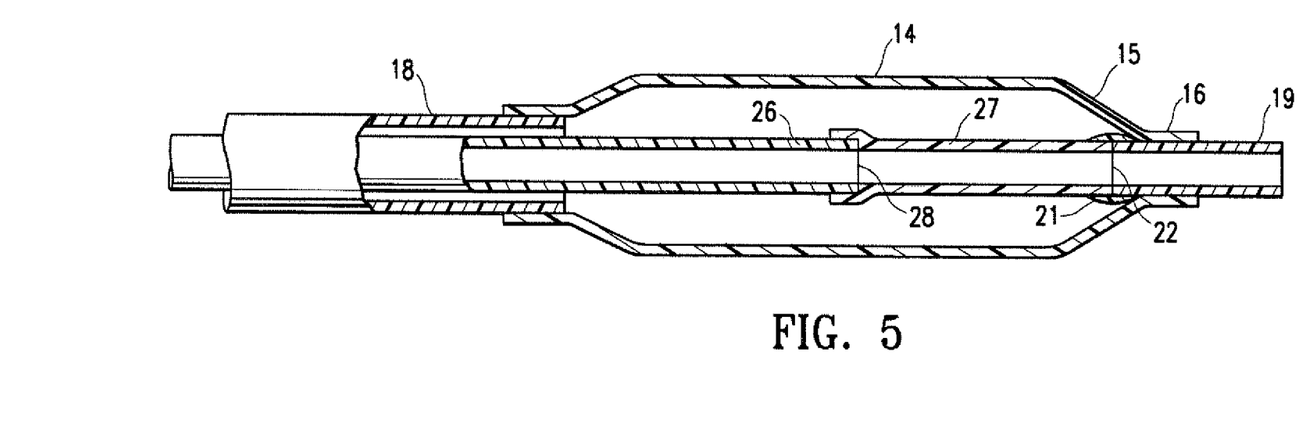
FIG. 5 illustrates an alternative embodiment of the catheter of FIG. 1, in which the inner tubular member includes a proximal member and a distal member joined together at about the center of the working length of the balloon.

In the embodiment of FIG. 1, the inner tubular member proximal and distal member junction 28 is a lap joint at the distal end of the working length of the balloon. However, the inner member can have a variety of suitable configurations including being a single unitary tube, or multiple tubes joined by end-to-end joints or lap joints. FIG. 5 illustrates an alternative embodiment similar to the embodiment of FIG. 1 except that the inner tubular member proximal member 26 and distal member 27 are joined together at about the center of the working length of the balloon 14.

Figure 6:
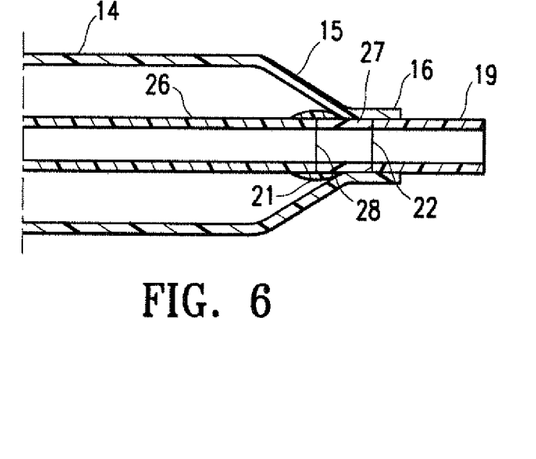
FIG. 6 illustrates an alternative embodiment of the catheter of FIG. 1, in which the distal coupling band member surrounds a junction between the proximal and distal members of the inner tubular member.

In the embodiment of FIG. 1, the distal coupling band member 21 surrounds the junction 22 of the distal member 27 and the distal tip member 19. FIG. 6 illustrates an alternative embodiment which is similar to the embodiment of FIG. 1 except that the distal coupling band member 21 surrounds a junction 28 between the proximal and distal members 26, 27 of the inner tubular member 18. In the embodiment illustrated in FIG. 6, the balloon distal skirt section 16 surrounds the junction 22 between the distal tip member 19 and the distal member 27, although in an alternative embodiment (not shown), the junction 22 between the distal tip member 19 and distal member 27 is proximal to the balloon distal skirt section 16, with a coupling band member surrounding one or both of the junctions 22, 28.

Figure 7:
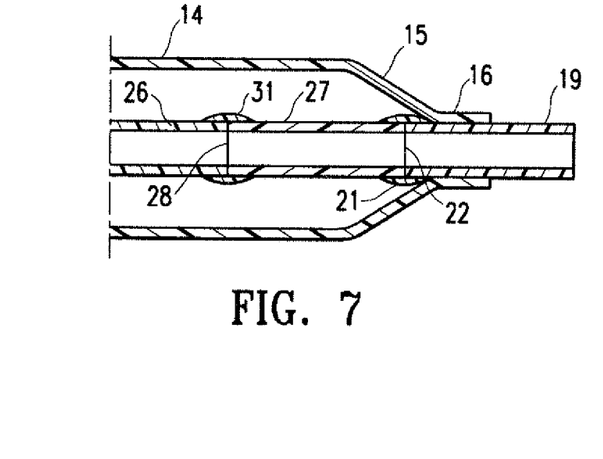
FIG. 7 illustrates an alternative embodiment of the catheter of FIG. 1, in which the catheter includes a proximal coupling band member surrounding the bond between the proximal and distal members of the inner tubular member.

FIG. 7 illustrates an alternative embodiment similar to the catheter of FIG. 1 except that the catheter includes a proximal coupling band member 31 surrounding the bond 28 between the proximal and distal members 26, 27 of the inner tubular member 18. In the illustrated embodiment, the proximal coupling band member 31 is at the center of the working length of the balloon 14, although the proximal coupling band member 31 and inner member junction 28 there under can be at a variety of suitable longitudinal locations along the shaft, typically within the inflatable interior of the balloon 14. For example, in alternative embodiments (not shown) the proximal coupling band member 31 and inner tubular member junction 28 there under are located at the distal end of the working length of the balloon 14 (at the proximal end of the distal cone section 15), or along the distal cone section 15 of the balloon 14.

In a presently preferred embodiment the coupling band members 21, 31 are formed of a polyether block amide (PEBAX) copolymer. However, the coupling band members 21, 31 can be formed of a variety of suitable polymeric materials, which are preferably fusion bond compatible with the outer layers of the underlying tubular members, and which include polyamides, polyurethanes, high density polyethylene (HDPE), ultrahigh molecular weight polyethylene (UHMWPE), and polyimide. In an embodiment in which the proximal coupling band member 31 is located at the working length of the balloon 14, it is preferably a polymeric material loaded with radiopaque material, to function as a radiopaque marker band. The distal coupling band member 21 is preferably not radiopaque, due to its location.

Figures 8, 9A, 9B, 9C:
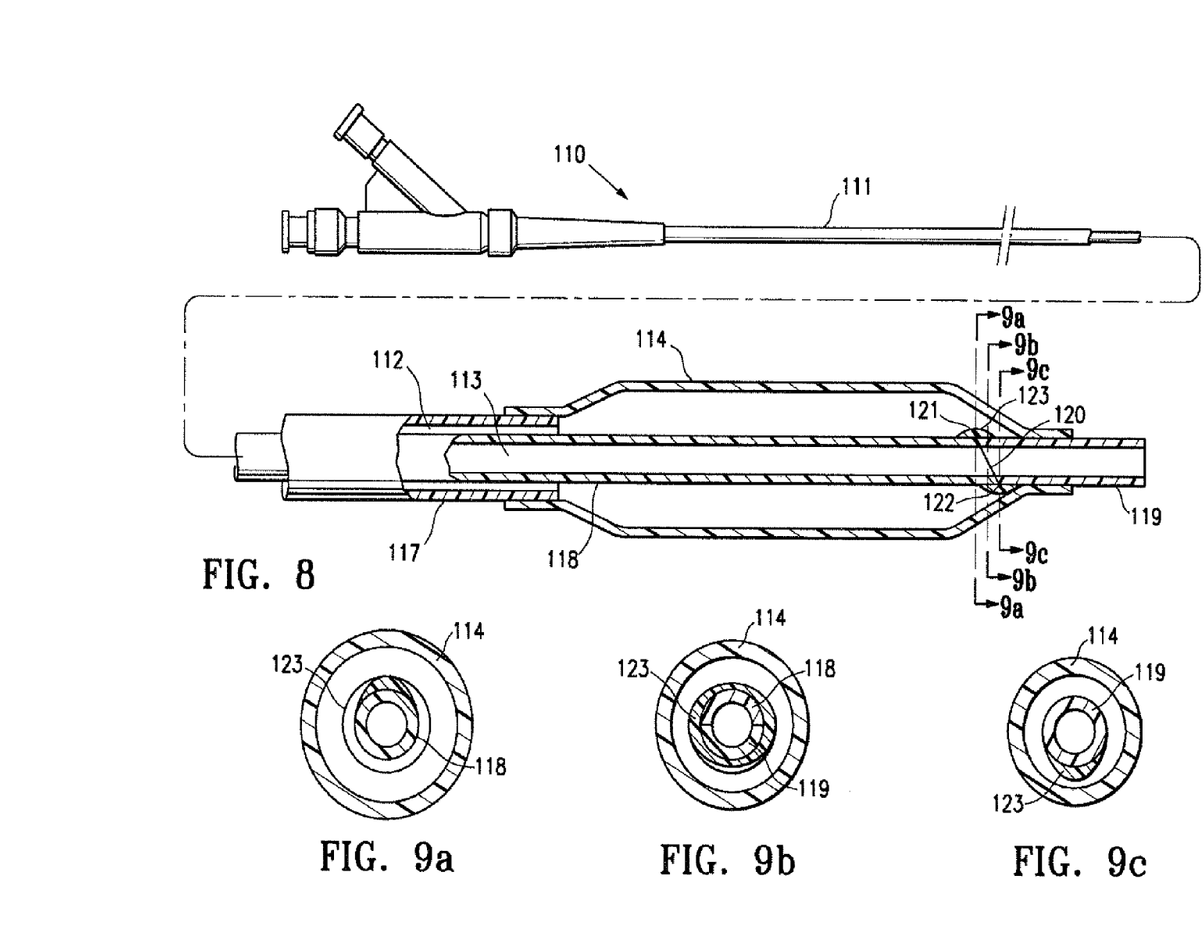
FIG. 8 is an elevational view, partially in section, of an alternative catheter embodying features of the invention, having shaft segments joined by a diagonal seam and a diagonally extending coupling band member.
FIGS. 9a, 9b, and 9c are transverse cross sections of FIG. 8, taken through lines 9a-9a, 9b-9b, and 9e-9c, respectively.

FIG. 8 illustrates an alternative catheter 110 embodying features of the invention, having shaft segments joined by a diagonal seam 120 and a diagonally extending coupling band member 123 surrounding the diagonal seam. In the illustrated embodiment, the catheter 110 is a balloon catheter generally comprising an elongated shaft 111 having a proximal end, a distal end, an inflation lumen 112, a guidewire receiving lumen 113, and a balloon 114 on a distal shaft section having an interior in fluid communication with the inflation lumen 112. In the embodiment of FIG. 8, the shaft 111 comprises an outer tubular member 117 with the annular inflation lumen 112 therein, an inner tubular 118 with the guidewire lumen 113 therein, and a distal tip member 119 (e.g., a soft tip member) which is secured to a distal end of the inner tubular member 118 to thereby define a distal portion of the guidewire lumen 113 and which is formed at least in part of a softer polymeric material than the distal end of the inner tubular member 118. Although illustrated in a balloon catheter 110, it should be understood that the diagonal seam 120 of the invention can be used to join shaft segments of a variety of suitable catheters including stent and drug delivery catheters (with or without a balloon), and the like.

The distal tip member 119 has a diagonally extending proximal end bonded to a diagonally extending distal end of the inner tubular member 118, such that the bond between the ends extends from a first side of the shaft diagonally to the opposite side of the shaft (i.e., diagonally across the guidewire lumen 113 defined by the tubular members 118, 119) to form diagonal seam 120. Because the seam 120 is diagonal, the proximal end 121 of the seam is at the first side of the shaft while the distal end 122 of the seam is at the opposite side of the shaft, and portions of the inner tubular member 118 radially adjacent to the proximal end 121 of the seam 120 (i.e., in a transverse cross section in a plane perpendicular to the shaft axis taken through the proximal end 121) are proximally spaced from longitudinally adjacent middle portions of the seam located between the ends 121, 122 of the seam 120. The diagonal seam 120 provides a gradual flexibility transition in which the material of the inner tubular member gradually gives way to the material of the soft distal tip member along the entire length of the bond (i.e., from the proximal end 121 to the distal end 122 of the bond). As a result, in contrast to a joint between tubular members with a straight cut end(s), the diagonal seam of the invention provides a less abrupt change in stiffness along the axial (longitudinal) direction. Additionally, the diagonal seam results in a stronger junction than a straight cut butt, lap, or otherwise coupled seam of similar diameter, as discussed in more detail below.

In the embodiment of FIG. 8, the diagonally extending ends are butt joined together (i.e., without overlapping the inner and outer surfaces of the tubular members 118, 119). The diagonal seam provides a strong bond. Specifically, unlike a conventional butt joint between straight ends, the diagonally extending ends provide a longer bond length and correspondingly larger bond cross-sectional area for bonding together. The longer bond length of the diagonal butt joint bond is particularly advantageous in an embodiment in which one or both of the tubular members 118, 119 is a multilayered tubular member having a layer of material which is not readily bondable. For example, the inner tubular member 118 preferable has an outer layer of a material such as a polyamide which facilitates bonding to adjacent components, and an inner layer of a lubricious/low friction material such as HDPE which has a relatively low surface energy and which is not readily fusion or adhesively bonded to other polymeric materials such as polyamides commonly used to form soft tip members. Thus, the diagonal butt joint bond increases the surface area of the bondable outer layer material contributing to the bond, thereby providing a stronger bond to the soft distal tip member formed at least in part of a material compatible with the outer layer material of the inner tubular member.

In a method of forming the diagonal seam 120, the ends of the inner tubular member 118 and distal tip member 119 are made to taper diagonally at the same angle, typically by cutting or otherwise mechanically removing material from the end of each tubular member 118, 119. The resulting diagonally extending surfaces are put together such that the inner and outer surfaces of the inner tubular member 118 are aligned with the inner and outer surfaces, respectively, of the distal tip member 119. The mating surfaces are then bonded together to form the diagonal bonded seam 120, typically by heat fusing by focusing a heat source on the mating surfaces to soften the polymeric materials and then allowing the heated materials to cool and solidify together. Alternatively, an adhesive can be provided between the mating surfaces, such that the resulting diagonal seam 120 is an adhesive bond. The terminology "bonded seam" should be understood to refer to a bond formed between two separately formed tubes, and not a bond which naturally results during formation thereof such as by coextrusion of a multilayered/multisectioned shaft. The tubular members are typically formed by hot melt extrusion, and thus the bonded seam is formed after extrusion of the tubular members. A mandrel is typically provided inside the tubular members 118, 119 during bonding to support the luminal shape, and a heat shrink tube (not shown) is typically provided on the tubular members 118, 119 at the location of the mating surfaces, to facilitate forcing the mating surfaces together during bonding, and which is removed and discarded after formation of the bond. The length of the resulting diagonal seam can vary depending on characteristics such as the location of the seam 120 along the length of the catheter, the nature of the tubular members bonded together thereby, and the desired characteristics of the transition formed thereby. The diagonal butt joint seam 120 located in the balloon interior or elsewhere along the length of the catheter generally has a length of about 0.5 mm to about 40 mm, more typically about 20 to about 30 mm.

The diagonal butt joint bond 120 does not increase the profile of the shaft. The outer surface of the inner tubular member 118 aligns with the outer surface of the soft tip member 119 prior to the bonding. In contrast, if the inner tubular member 118 had a conventionally tapered distal end (i.e., which decreases the outer diameter of the tubular member by tapering uniformly around the entire circumference of the tubular member), the proximal end of the soft tip member would have to flare outwardly to bond by overlapping the tapered distal end, and thus would increase the profile of the shaft therealong. Moreover, compared to bonding to a conventionally tapered end, the diagonal ends facilitate forming a relatively long bond length because the diagonal seam 120 extends diagonally across the shaft lumen (e.g., guidewire lumen 113) from one side to the opposite side of the shaft 111.

As with the embodiment of FIG. 1, coupling band member 123 covers the seam between the inner tubular member 118 and the soft distal tip member 119. In the embodiment of FIG. 8, the coupling band member 123 extends diagonally, preferably at an angle corresponding to the diagonal butt joint seam 120. Specifically, the diagonally extending coupling band member 123 surrounds the diagonal seam 120 on an outer surface of the tubular members 118, 119, and has diagonal proximal and distal ends extending diagonally across the inner diameters of the tubular members 118, 119. The discussion above relating to the materials of the coupling band member of the embodiment of FIG. 1 applies to diagonal coupling band member 123. FIGS. 9a-9a, 9b-9b, and 9c-9c illustrate transverse cross sections of the catheter of FIG. 8 taken along lines 9a-9a, 9b-9b, and 9c-9c, respectively. The diagonal coupling band member 123 extends fully around the circumference of the shaft 111, to reinforce the diagonal seam 120, but provides a more gradual change in stiffness and profile than a coupling band having straight end(s). In the illustrated embodiment, the distal end of the diagonal coupling band member 123 abuts the inner surface of the balloon at a distal end of the distal cone section. However, the location of the diagonal coupling band member 123 (and diagonal seam 120 there under) can vary.

Figure 10:
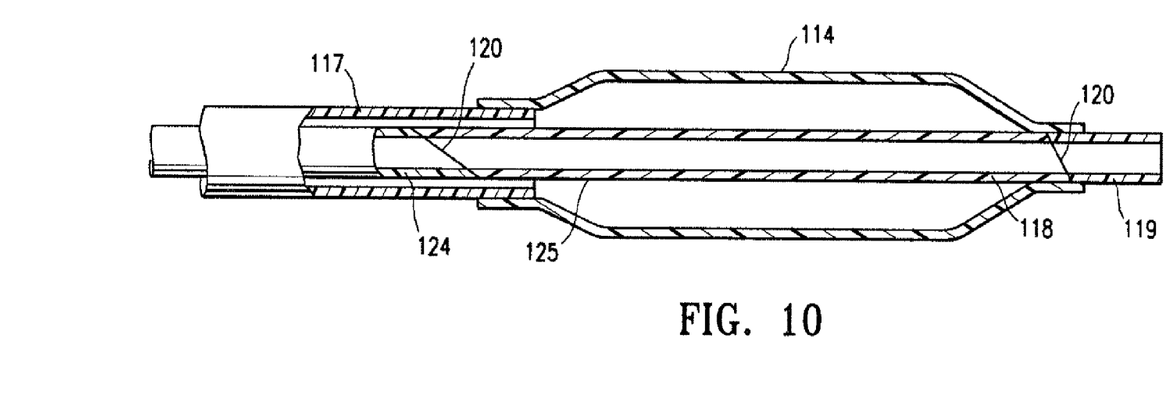
FIG. 10 illustrates an alternative embodiment of the invention, having a first diagonal seam, and a second diagonal seam between two shaft segments located proximal to the soft tip member of the catheter.

Although the embodiment illustrated in FIG. 8 has the diagonal seam 120 between the inner tubular member and the distal tip in the balloon interior, it should be understood that the diagonal seam 120 can be used at any location along the length of the catheter 110 from the proximal to the distal end of the catheter, and including between segments of the outer tubular member 117 of the shaft 111 in addition to or as opposed to the inner tubular member 118. One embodiment has multiple flexibility transitions provided by multiple diagonal seams in accordance with the invention at different longitudinal locations along the shaft. FIG. 10 illustrates an alternative embodiment of the invention in which the shaft 111 has a first diagonal seam 120 which is between the inner tubular member 118 and tip member 119 and which is located under the distal skirt of the balloon 114, and a second diagonal seam 120 between two segments 124, 125 of the inner tubular member 118 located proximal to the soft tip member 119. In the embodiment of FIG. 10, the two diagonal seams 120 extend diagonally at different angles but toward the same side of the shaft (circumferential orientation). In alternative embodiments the seams 120 have the same angle and/or a different circumferential orientation. Although the distal diagonal seam 120 is illustrated in FIG. 10 with a relatively short length that is entirely under the balloon distal skirt section 16, in alternative embodiments the distal diagonal seam 120 has a longer length/more acute angle such that it extends from under the skirt 16 to a location proximal and/or distal of the balloon distal skirt section 16. For example, in one embodiment, the diagonal seam 120 located in part under the balloon distal skirt section 16 has a proximal end 121 located at the proximal end of the cone section of the balloon (at the distal end of the working length of the balloon). As a result, in one embodiment, the length of a proximal end section of the distal tip from the proximal to the distal end of the diagonal seam is longer than the length of a distal section of the distal tip from the distal end of the diagonal seam to the distal end of the distal tip member 119.

Figure 11:
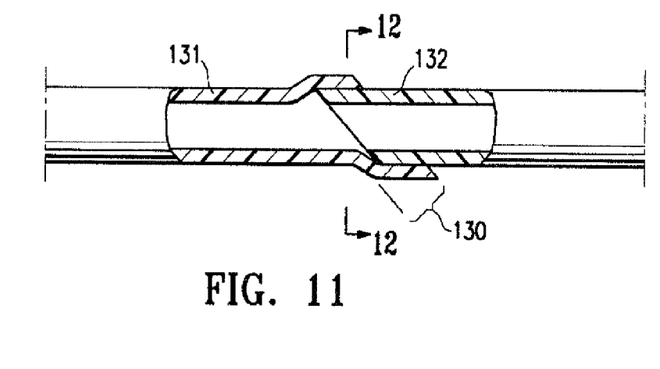
FIG. 11 illustrates an alternative embodiment of the invention, having a diagonal seam formed by shaft segments with overlapping diagonal ends.
Figure 12:
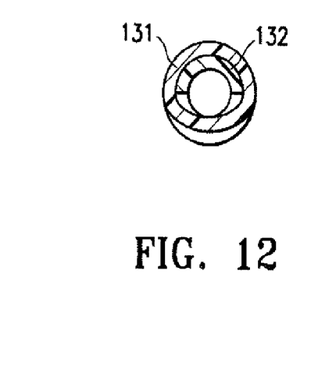
FIG. 12 is a transverse cross section of FIG. 11, taken through line 12-12.

FIG. 11 illustrates an alternative embodiment in which the catheter shaft 111 has a diagonal seam 130 formed by tubular members 131, 132 with overlapping diagonal ends. The lap-joined diagonal seam 130, although not as low profile as the butt-joined diagonal seam 120, still provides an improved flexibility transition in which the overall volume of softer material of the distal tubular member 132 gradually increases along the entire length of the bond. The stiffness increase caused by overlapping the ends of the tubular members is more gradual than the stiffness increase that would have resulted if one or both mating ends of the tubular members 131, 132 had a conventional straight end. FIG. 12 is a transverse cross section taken through the diagonal bond between the diagonal ends of the tubular members 131, 132, along line 12-12 of FIG. 11.

In a presently preferred embodiment, the inner tubular member 118 is a trilayer tubular member having an inner layer typically formed of a lubricous material such as HDPE, a middle tie layer such as a functionalized polyolefin adhesive polymer, and an outer readily bondable layer such as a polyamide such as a nylon or a polyether block amide (PEBAX). The diagonal seam between two segments of the inner tubular member provides a stiffness transition typically by transitioning from a trilayer having an outer layer of a higher Shore durometer hardness material to a trilayer having an outer layer of a compatible but lower Shore durometer hardness material. For example, in one embodiment, the diagonal seam 120 is between a proximal segment 124 of a trilayer of HDPE, tie layer polymer, and PEBAX 63D outer layer to a distal segment 125 of a trilayer of HDPE, tie layer polymer, and PEBAX 35D outer layer, although a variety of suitable materials may be used. In the illustrated embodiment, the distal tip member 119 is a single layer tubular member, typically being formed of a polymer fusion bond compatible an adjacent layer of the inner tubular member 118. However, a variety of suitable tip members can be used including multilayer tip members. The distal tip member is generally configured to provide flexibility and is typically formed of a softer polymeric material than the adjacent section of the inner tubular member.

In one embodiment, the diagonal seam 120, 130 provides directionality to the bending of the shaft when the tubular members bonded together by the diagonal seam have a different flexibility. For example, the shaft 111 will bend/deflect towards the side of the diagonal seam having more of a lower Shore durometer hardness material than the opposite side of the diagonal seam. Thus, the shaft will curve inwardly on the side of the shaft having the proximal end 121 of the diagonal seam 120 between the inner tubular member 118 and the soft tip member 119 (formed at least in part of a polymeric material having a lower Shore durometer hardness than the inner tubular member 118). In an embodiment in which the tubular members are not of a different flexibility at the diagonal seam, the diagonal seam does not provide bending directionality, although the diagonal seam nonetheless provides the advantages of a strong but relatively low profile joint as discussed above.

The dimensions of catheters of the invention are determined largely by the size of the balloon and guidewire to be employed, the catheter type, and the size of the artery or other body lumen through which the catheter must pass, or the size of the stent being delivered. Typically, the outer tubular member 17/117 has an outer diameter of about 0.025 to about 0.04 inch (0.064 to 0.10 cm), usually about 0.037 inch (0.094 cm), and the wall thickness of the outer tubular member 17 can vary from about 0.002 to about 0.008 inch (0.0051 to 0.02 cm), typically about 0.003 to 0.005 inch (0.0076 to 0.013 cm). The inner tubular member 18/118 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10, 110 may range from about 100 to about 150 cm, and is typically about 143 cm. Preferably, balloon 14, 114 has a length about 0.8 cm to about 6 cm, and an inflated working diameter of about 2 to about 10 mm.

Although the tubular members of the shafts 11, 111 are illustrated as having uniform inner and outer diameters and wall thicknesses, it should be understood that they can have tapering inner or outer diameters at various locations along the length of the shaft. For example, the tip member 19, 119 can have a thinner wall thickness than the end section of the inner tubular member to be bonded thereto, in which case the inner surfaces are typically aligned and the outer surface of the inner member is caused to flow distally during bonding to smooth the outer surface at the junction.

The shaft outer and inner tubular members and tip member can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. The inner tubular member and outer tubular member are typically multilayered tubing, or sections of tubing joined end-to-end, as is conventionally known for balloon catheter shafts. Although the shaft is illustrated as having an inner and outer tubular member, a variety of suitable shaft configurations may be used including a dual lumen extruded shaft having a side-by-side lumens extruded therein. Although the embodiment illustrated in FIG. 1 is an over-the-wire type balloon catheter having the guidewire lumen extending from the guidewire distal port at the catheter distal end to a guidewire proximal port at the proximal end of the shaft, the catheter can alternatively be a rapid exchange catheter having a relatively short guidewire lumen extending from the distal end port to a guidewire proximal port spaced distally from the proximal end of the catheter shaft. Additionally, the outer tubular member typically includes supporting members including a high strength member such as a hypotube in the proximal shaft section and/or across the guidewire proximal port in the rapid exchange embodiment (not shown).

While the present invention is described herein in terms of certain preferred embodiments, those skilled in the art will recognize that various modifications and improvements may be made to the invention without departing from the scope thereof. For example, although illustrated in terms of embodiments in which the distal coupling band member is on the guidewire lumen-defining inner tubular member of the balloon catheter, the lumen surrounded by the distal coupling band member can have a variety of suitable designs and uses (e.g., drug delivery) in addition or as an alternative to use as a guidewire lumen. Similarly, the diagonal seam can be used to join shaft segments having a variety of uses and locations along a shaft of a variety of suitable catheter types. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter comprising:
   an elongate tubular shaft having a proximal portion and a distal portion, the elongate tubular shaft including an inner tubular member having a distal length extending distally from the distal portion of the elongate tubular shaft, the elongate tubular shaft having an inflation lumen and a guidewire lumen defined therein, the guidewire lumen extending along at least the distal length of the inner tubular member;
   a distal end section coupled to a distal end of the inner tubular member, the distal end section having a proximal end and a distal end, wherein the distal end section includes a distal inner member having a proximal end and a distal end, and a distal tip member having a proximal end and a distal end, the proximal end of the distal inner member coupled to the distal end of the inner tubular member and the proximal end of the distal tip member coupled to the distal end of the distal inner member; and
   a balloon having a proximal portion, a distal portion and a working length therebetween, the proximal portion of the balloon sealingly coupled to the distal portion of the elongate tubular shaft, the distal portion of the balloon sealingly coupled to the distal end section, the balloon defining an inner chamber in fluid communication with the inflation lumen;
   wherein the proximal end of the distal end section is disposed within the inner chamber.

2. The balloon catheter according to claim 1, wherein the inner tubular member and the distal end section are coupled by at least one of a lap-joint or a butt-joint.

3. The balloon catheter according to claim 1, wherein the distal end section is more flexible than the inner tubular member.

4. The balloon catheter according to claim 1, wherein the distal end section comprises at least in part a softer polymeric material than a material of the inner tubular member.

5. The balloon catheter according to claim 1, wherein the distal tip member comprises at least a first material and the distal inner member comprises at least a second material, wherein the first material is more flexible than the second material.

6. The balloon catheter according to claim 5, wherein the first material of the distal tip member comprises a polymeric material.

7. The balloon catheter according to claim 5, wherein the inner tubular member comprises at least a third material, wherein the second material is more flexible than the third material.

8. The balloon catheter according to claim 1, wherein the distal tip member comprises a Shore durometer hardness ranging approximately from 35D to 70D.

9. The balloon catheter according to claim 1, wherein the distal inner member and the distal tip member are coupled by a butt-joint.

10. The balloon catheter according to claim 1, wherein the distal inner member and the distal tip member are coupled by a bond along a diagonal seam therebetween.

11. The balloon catheter according to claim 10, wherein the diagonal seam is disposed in the inner chamber of the balloon.

12. The balloon catheter according to claim 1, wherein the distal tip member has a generally uniform cross section.

13. The balloon catheter according to claim 1, wherein the proximal end of the distal tip member comprises a thickness less than a thickness of the distal end of the distal inner member.

14. The balloon catheter according to claim 1, further comprising a distal coupling band member coupled to the distal end of the distal inner member and the proximal end of the distal tip member.

15. The balloon catheter according to claim 1, wherein the distal end of the distal tip member has an atraumatic configuration.

16. The balloon catheter according to claim 1, wherein an outer diameter of the inner tubular member decreases uniformly in the distal portion.

17. The balloon catheter according to claim 1, further comprising a medical device coupled to the balloon.

18. The balloon catheter according to claim 1, further comprising at least one radiopaque marker coupled to the inner tubular member.

19. The balloon catheter according to claim 1, wherein the proximal portion of the balloon includes a proximal skirt section and a proximal cone section and the distal portion of the balloon includes a distal skirt section and a distal cone section.

* * * * *